United States Patent [19]

Segar et al.

[11] 4,380,802
[45] Apr. 19, 1983

[54] ELECTRONIC CALORIE COUNTER

[75] Inventors: Richard B. Segar, Annapolis, Md.; Lewis C. Marascalco, Pittsburgh, Pa.

[73] Assignee: GPD Inc., Mitchellville, Md.

[21] Appl. No.: 165,268

[22] Filed: Jul. 2, 1980

Related U.S. Application Data

[63] Continuation-in-part of Ser. No. 907,338, May 18, 1978, Pat. No. 4,212,079.

[51] Int. Cl.³ .............................................. G06F 15/42
[52] U.S. Cl. ..................................... 364/900; 364/413
[58] Field of Search ... 364/200 MS File, 900 MS File, 364/413, 415, 715, 550

[56] References Cited

U.S. PATENT DOCUMENTS

| | | | |
|---|---|---|---|
| 3,593,313 | 7/1971 | Tomaszewski et al. | 364/200 |
| 4,100,401 | 7/1978 | Tutt et al. | 364/415 X |
| 4,101,071 | 7/1978 | Brejnik et al. | 364/415 X |
| 4,192,000 | 3/1980 | Lipsey | 364/415 |
| 4,212,079 | 7/1980 | Segar et al. | 364/900 |
| 4,244,020 | 1/1981 | Ratcliff | 364/413 |

OTHER PUBLICATIONS

"Diet Computer," Wall Street Journal, Mar. 22, 1979.

Primary Examiner—Raulfe B. Zache
Attorney, Agent, or Firm—Armstrong, Nikaido, Marmelstein & Kubovcik

[57] ABSTRACT

A net calorie calculating apparatus is provided for calculating the calories burned by a person, the calories consumed by the person and the difference therebetween. The apparatus includes a calculator for performing mathematical calculations, the calculator including a keyboard and a display. A first memory is coupled to the calculator and stores rate data representing the rate of calories burned for different predetermined human activities. A second memory is coupled to the calculator and stores calorie content data representing the number of calories per unit of various predetermined kinds of food. A program memory stores programs for controlling the calculator for the calculation of calorie burn rate, total calories burned and net calories, and an interface couples the program memory to the calculator. A control means controls the operation of the program memory to inititate various calculations in the calculator.

13 Claims, 3 Drawing Figures

ELECTRONIC CALORIE COUNTER

RELATED APPLICATIONS

This application is a continuation-in-part of our previously filed application Ser. No. 907,338, filed May 18, 1978 now U.S. Pat. No. 4,212,079.

BACKGROUND OF THE INVENTION

1. Field of the Invention

The present invention is directed to a calorie monitoring and calculating device and more particularly to a calorie monitoring and calculating device which calculates the calorie intake from consumption by the person and the calories burned by the person on a real time basis and which displays the difference therebetween.

2. Description of the Prior Art

In order to effectively control one's weight, it is necessary to provide a proper balance between the caloric input and the number of calories burned. For example, if an individual desires to lose weight, then it is necessary for the number of calories consumed or the calorie intake to be less than the number of calories which are burned as a result of the normal activity and exercise by the individual. If the individual wishes to merely maintain his weight, then it is necessary that the number of calories consumed be approximately equal to the number of calories burned.

In order to effectively maintain the proper balance, an individual must be able to record the number of calories consumed and to calculate the number of calories burned. In recording the number of calories consumed, the individual must have some information readily available which indicates the number of calories per unit quantity of various types of food, and must also have some means for keeping a running total of the number of calories consumed over a period of time, such as a day, several days, a week, etc.

In calculating the number of calories burned, the individual must take into consideration the type of activity in which he is engaged. Naturally, the number of calories burned in a function of the level of activity. Furthermore, the number of calories burned is also dependent upon the particular characteristics of the individual, such as the weight, age and sex of the individual.

One prior art type of calorie calculating device is disclosed in U.S. Pat. No. 4,100,401. This patent is directed to a calorie counter which is incorporated into an electronic wristwatch, which enables the user to enter caloric intake information and determine a caloric rate expenditure and then to calculate the excess of calorie intake over calorie expenditure. This patent does not have any provision for storing data related to the number of calories per unit of various types of food, nor does it have any provision for storing data related to the rate at which calories are burned in relation to the type of physical activity of an individual. The device of this patent thus requires a user to either memorize large quantities of data or to carry with him booklets or other types of printed material which contain this data. Furthermore, in order to make these calculations, it is necessary to read the printed material and then enter this data into the calorie counter.

Another prior art calorie calculating device is shown in U.S. Pat. No. 4,101,071. This prior art device is used by an individual to calculate and provide an indication of the total calories burned by the individual. The device disclosed in this patent is incorporated into a wristwatch. The wristband includes a detector for detecting the pulse of the individual. The individual's pulse rate is then converted into calories burned data, with the number of calories burned being dependent upon the pulse rate.

This prior art device has the disadvantage that the number of calories burned is not directly proportional to the pulse rate. Factors such as weight, age and sex are important in the calculation of the calorie burn rate for a particular individual. Furthermore, this prior art device has no provision for calculating the number of calories consumed and providing an output indicative of the difference between the number of calories consumed and the number of calories burned.

SUMMARY OF THE INVENTION

It is the primary object of the present invention to provide a calorie monitoring and calculating device which provides a display of the difference between the calories consumed and the calories burned by an individual on a real time basis.

It is another object of the present invention to provide a calorie monitoring and calculating device which calculates the number of calories burned by an individual in the performance of various different physical activities having different exertion levels and to perform this calculation at predetermined short time intervals to thereby provide a real time value of the number of calories burned by the individual.

It is another object of the present invention to provide a calorie monitoring and calculating device which stores data related to the rate of calories burned for the particular individual for predetermined types of physical activity, and which performs the calculation of the calorie burn rate in response to the input of a short alpha-numeric indication of the type of activity which is being performed.

It is still a further object of the present invention to provide a calorie monitoring and calculating device which stores the number of calories contained in unit quantities of predetermined types of food and which calculates the number of calories consumed when food is eaten by entering into the device a short alpha-numeric indication of the type of food consumed and the quantity consumed.

It is still a further object of the present invention to provide a calorie monitoring and calculating device which provides an indication when the number of calories burned exceeds the number of calories consumed.

The present invention provides a calorie monitoring and calculating device for calculating the calories burned by a person, the calories consumed by a person and the difference therebetween. The device comprises a calculator for performing mathematical calculations, the calculator including a keyboard and display. A first memory is coupled to the calculator for storing rate data representing the rate of calories burned for different predetermined human activities for the particular person using the device. The data stored in this memory can be retrieved for use in calculations by entering an alpha-numeric indication of the type of human activity into the calculator keyboard. A second memory is provided which stores calorie content data representing the number of calories per unit of various predetermined kinds of food. This data can be retrieved by entering into the calculator keyboard an alpha-numeric indication of the kind of food. The device includes a program memory which stores a plurality of programs for controlling the calculator for the calculation of the calorie burn rate, the total calories burned and the net calories, which is the difference between the total calories burned and the total calories consumed. An interface couples the program memory to the calculator and a control circuit controls the operation of the program memory.

The control circuit includes switches for selecting the calculations to be performed, and a timer for performing the calories burned calculation at predetermined time intervals.

DETAILED DESCRIPTION OF THE PREFERRED EMBODIMENTS

Figure 1:
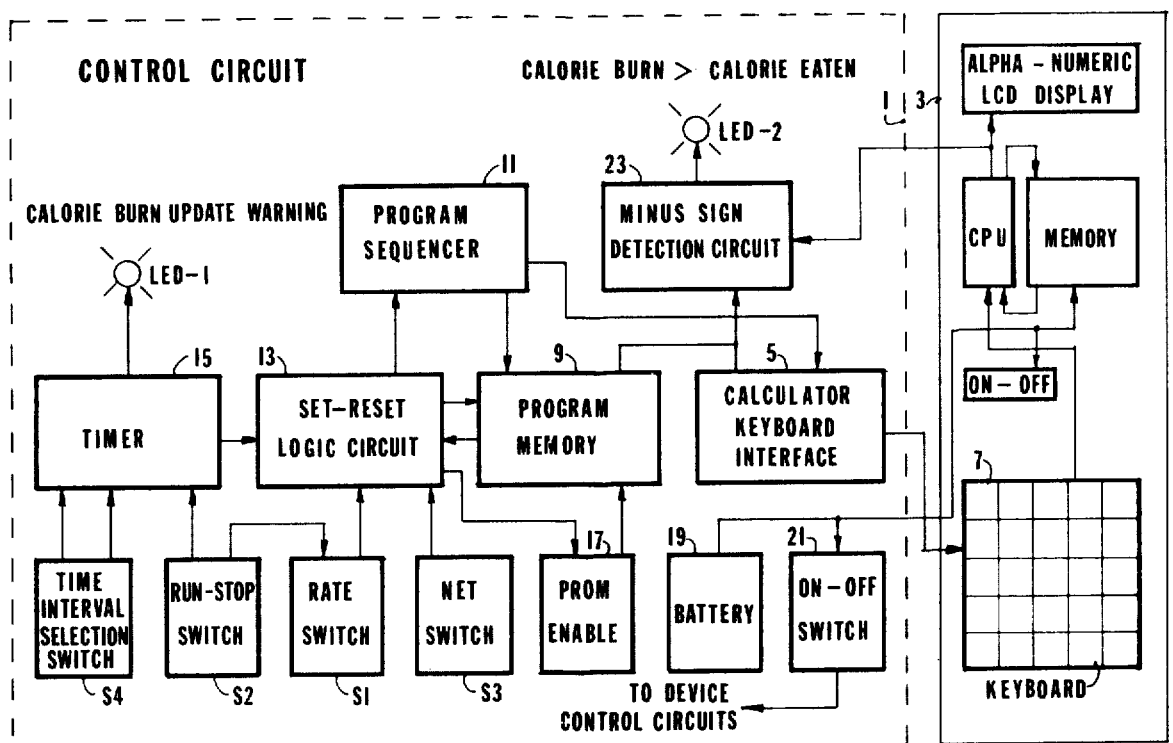
FIG. 1 is a functional block diagram of the calorie monitoring and calculating device of the present invention.

The calorie monitoring and calculating device of the present invention provides a means for a person, on a real time basis, to keep a running total of the calories that he has burned while simultaneously providing a means for keeping a running total of the calories in the food that the person has eaten. The number of calories burned is subtracted from the number of calories eaten and an indication is provided of this net difference.

The present invention uses a commercially available calculator with an alpha-numeric calculator directory, such as a Radio Shack Model EC-4002. A calculator of this type has a conventional four function calculator with memory and thirty alphanumeric memories capable of storing up to thirty individual words consisting of letters and associated numbers. Data is entered into the device via the calculator keyboard and control switches are provided for initiating various calorie monitoring and calculating functions. The device can also function as a standard calculator.

In order to perform its calorie monitoring and calculating function, the device of the present invention is programmed to perform several necessary calculations.

The calorie burn, or metabolic rate, represents the rate at which the human body is consuming energy per unit of time. This rate differs for every individual, and before the total calories burned for a length of time can be calculated for an individual, the calorie burn rate for that individual must be calculated. The person's calorie burn rate is a function of that person's activity level, weight, age, sex and other miscellaneous factors. Tables are available for calorie burn rates for different activity levels per unit of weight. Multiplying a rate for a specific activity level (i.e., calories per unit time per pound) by the weight of the person yields calories burned per unit of time for the person. This burn rate is then modified by multiplying by a constant which is based upon the individual's age, sex and other miscellaneous factors. The modifier is a fractional number that lowers the burn rate slightly.

The burn rate for a particular individual is calculated by first storing the person's weight in the alpha-numeric memory of the calculator. The data is entered into the calculator using the calculator keyboard. A constant modifier, which is based upon the person's age, sex and other miscellaneous factors is also stored in the alpha-numeric calculator memory with entry by using the keyboard. The activity level rate is also stored in the calculator's alpha-numeric memory by entry through the keyboard. The numerical activity level rate is stored with alphabet characters related to the activity so that it can be recalled from memory using the alphabet character. Table 1 below lists examples of activity level rates per unit of weight for various activities.

TABLE 1

| Activity (6 letters maximum) | Value |
|---|---|
| Sleep | .0619 calories/lb./8 minutes |
| Office (work at the office) | .1589 calories/lb./8 minutes |
| Mowing | .0271 calories/lb./minute |
| Jog | .0713 calories/lb./minute |

Typically, four to six activities and their level rates are stored in the calculator memory. These rates would correspond to the activities which the user probably would be engaged in over a period of time. If the activities change, such as when the user goes on vacation, for example, then the activities stored in the memory can be changed or new activities can be added. This is done by using the calculator keyboard.

A person selects his activity level by using the calculator keyboard to enter the alphabet letters corresponding to the activity which he is about to engage in. A control switch designated "Rate" is then operated momentarily and the control circuit operation is initiated. The control circuit generates a program for controlling the calculator to enable the calculator to calculate a rate value for the particular individual, taking into consideration the individual's weight, age, sex and other miscellaneous factors which have already been stored in the alpha-numeric calculator memory. The calculated rate is then stored in the alpha-numeric calculator memory for use in the calculation of the total calories burned.

The total calories burned by a person during the time at which they are performing a particular activity is calculated by adding a calorie burn rate, which is a number of calories per unit of time, to a running total at intervals corresponding to the predetermined unit of time. Depending upon the particular activity level, this may be one minute intervals, or eight minute intervals, or any other interval which may be desirable. Longer intervals are used for activities such as sleep or office work, so that this calculation is not made as often and, therefore, power derived from a source such as batteries can be preserved.

To calculate the calories burned, a person selects the time interval selection switch, and then places a control switch designated "Run-Stop" to the "Run" position. The control circuit includes a clock circuit and begins timing the predetermined time interval. At the conclusion of the time interval, a signal is produced which generates a program from a program memory to calculate the calories burned by adding a number of calories per unit time based upon the calculated rate for the selected activity level stored in the calculator to a total calories burned stored in memory, and this new total calories burned replaces the old total calories burned in the memory.

If a person using the device changes his activity, then the Run-Stop switch is switched to Stop, the alphabet letters corresponding to the new activity are entered into the keyboard, the Rate switch is activated and a new rate is calculated. The user then turns the Run-Stop switch to Run, and the total calories burned are calculated based upon the new activity.

The calculator is also used to calculate and store the calories consumed or eaten by an individual. As mentioned above, the alpha-numeric calculator memory stores the number of calories per unit of quantity for various types of food. Each type of food is stored with a numeric value, and alphabet letters corresponding to the food. When a person consumes a particular kind of food, the appropriate alphabet letters are keyed in, using the calculator keyboard and the number of calories corresponding to that type of food is read from the memory and then added to a running total of calories consumed, which is stored in another of the calculator memories. The new total is substituted for the old total in the calculator memory. The total calories consumed or eaten can be displayed at any time by merely reading the memory in which the total value is stored.

The net calories is the difference between the calories burned by the person as a result of all the different activities which that person may perform over a given period of time and the total calories consumed or eaten during that period of time. To perform the net calorie calculation, a control switch indicated "Net" in the control circuit is activated. This initiates the operation of the control circuit to generate a program for controlling the calculator for the calculation of the difference between the calories consumed and the calories burned. If the total calories burned within the given time period is greater than the total calories consumed within that period, then the difference would be negative. The value displayed on the calculator display would then include a minus sign and, in addition, an indicator light flashes so that the user is aware that he is burning more calories than he is consuming.

Figure 3:
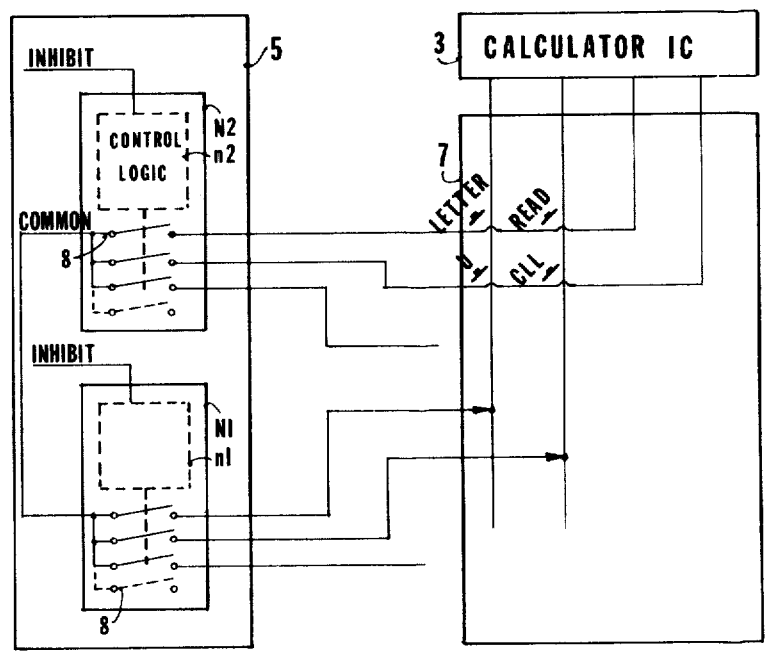
FIG. 3 is a schematic diagram representing the typical keyboard interface arrangement used with the present invention.
Figure 2:
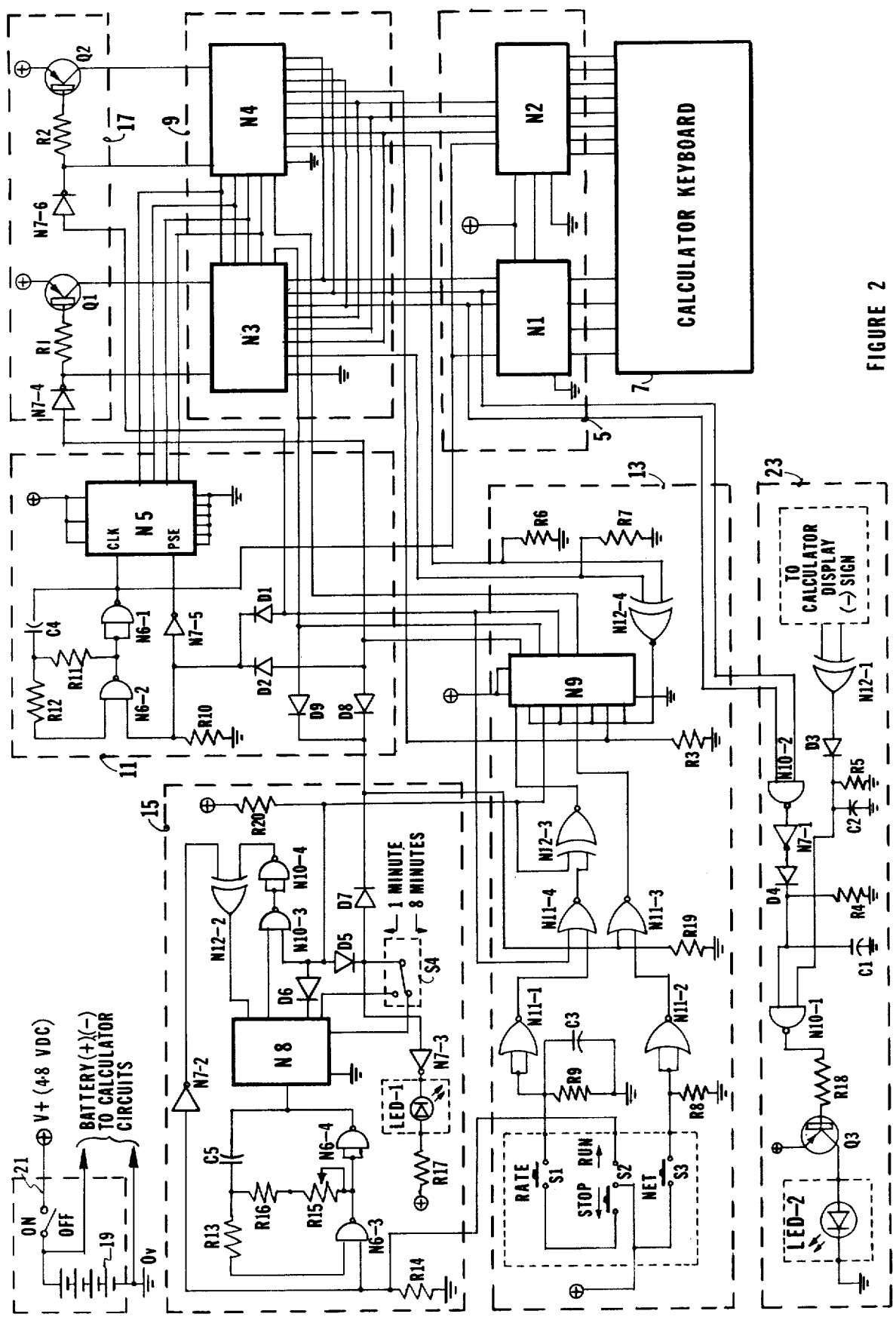
FIG. 2 is a schematic circuit diagram of the control circuit of the calorie monitoring and calculating device of the present invention.

Referring to FIGS. 1-3, control circuit 1 is connected to a calculator 3. The calculator keyboard interface 5 is connected to keyboard 7 of calculator 3. Keyboard interface 5 includes two IC's N1 and N2. As shown in FIG. 3, N1 and N2 are connected to the keyboard 7 in a manner which is equivalent to eight single pole switches 8, all of which have one side tied to a common input. The closure of any one of the switches is directly related to the binary four-bit address word sent to the control logic input n1 or n2 of N1 or N2. The outputs of N1 and N2 are connected to the keyboard in a row-by-column matrix such that a particular address word at their input closes the correct pair of switches to activate a particular keyboard input, the same as if the key itself had been depressed.

The sequence of steps necessary to perform the various calculations by the calculators 3 are stored in the program memory 9 which includes programmable read-only memory devices N3 and N4. The output of the program memories N3 and N4 are connected to the calculator keyboard 7 through the keyboard interface 5. A program stored in the program memory 9 is read out and applied to the keyboard 7 through keyboard interface 5 by sequentially changing the address input to the program memory 9.

Program sequencer circuit 11 is connected to the program memory 9 for addressing the input of program memory 9. The program sequencer 11 includes a gated oscillator N6-1 and N6-2 and a counter N5. The output of the counter N5 is the input address to the program memories N3 and N4, such that the program memories generate the program sequence of proper address words to the interface circuits N1 and N2.

Set-reset logic circuit 13 includes logic components, the main element of which is N9, which consists of four set-reset flip-flops. The set-reset logic circuit 13 also includes Rate switch S1, Stop-Run switch S2 and Net switch S3. The Rate switch S1 is activated to initiate the calorie burn rate calculation when switch S2 is in the "Stop" position. When switch S2 is switched to the "Run" position, the calories burned per time interval are calculated with the time intervals being timed by main timer 15.

Program memory enable circuit 17 is coupled to the set-reset logic circuit 13 and to the program memory 9. Program memory enable circuit 17 functions to provide power to the program memories only if it is energized by the set-reset logic circuit during a rate, burn or net calculation. This conserves battery power, since there is no need to provide energy to the program memory 9 when no calculations are being made.

When Run-Stop switch S2 is in the "Run" mode, the timer circuit 15 provides timing pulses at predetermined time intervals, such as for example, one minute and eight minute intervals. The time intervals can be selected using Time Interval Selection switch S4. The timing pulse output from the timer 15 is applied to the set-reset logic circuit 13 to initiate the calorie burn update program.

The timer 15 consists of a gated oscillator N6-3 and N6-4 and a binary counter N8. The oscillator is gated on by the Run-Stop switch S2, when it is switched to the "Run" mode. Prior to the timer 15 activating set-reset logic circuit 13, LED-1 is lit, indicating that the calorie burn update calculation is about to occur. If the device is being used as a normal four-function calculator, this use must be stopped so as not to interfere with the calorie burn updated calculations. LED-1 thus provides the necessary indication for the user to stop the normal four-function calculations.

Power is supplied to the device from a battery 19 through an On-Off switch 21.

The control circuit also includes a minus sign detection circuit 23. The minus sign detection circuit is connected to the calculator display, and detects the display of a minus sign. When the minus sign is detected, LED-2 is energized for approximately four seconds. LED-2 is self-flashing, and flashes on and off at about three Hertz. The minus sign detection circuit 23 is enabled by program memory 9 only at the end of a net calorie calculation in order to prevent LED-2 from flashing if a minus sign is used during normal arithmetic calculations by the calculator 3.

In performing a calorie rate calculation in the device of the present invention, the following conditions are assumed: the activity level rate values for various predetermined types of activities are stored in the alpha-numeric calculator memory; a modifier constant for the particular person using the device is stored in the alpha-numeric calculator memory; a weight value in pounds of the person using the device is stored in the alpha-numeric calculator memory; some calorie rate (for first time use, this could be simply 0) is stored in the alpha-numeric calculator memory; switch 21 is turned on; Run-Stop switch S2 is switched to the "Stop" mode; and calculator On-Off is "On". The user then depresses alphabet or letter keys corresponding to the activity in which he is about to engage such as, for example, MOWING. The Rate switch S1 is then momentarily depressed.

When Rate switch S1 is depressed, a logic 1 is applied to the input of NOR gate N11-1 and capacitor C3 is charged. The output of NOR gate N11-1 goes to logic 0 and is held there until C3 discharges through R9 below the threshold of the input of NOR gate N11-1. Thus, a momentary depression of the Rate switch S1 causes a logic 0 at the output of NOR gate N11-1 for approximately one second. The logic 0 output is applied to the input of NOR gate N11-4. If the other input of NOR gate N11-4 is also at logic 0, the output will go to logic 1. The logic 0 at the other input of NOR gate N11-4 indicates that the P3 output of circuit N9 is at logic 0, meaning that a net calculation is not in progress.

The logic 1 output of NOR gate N11-4 is applied to the input of EXCLUSIVE or (XOR) gate N12-3. This results in the output of XOR gate N12-3 switching to logic 1. A logic 1 at the input S1 of circuit N9 sets output P1 of circuit N9 to logic 1. The P1 output of circuit N9 will remain at logic 1 until the completion of the calorie rate calculation program.

A logic 1 through diode D8 to an input of NOR gate N11-3 prevents the closure of Net switch S3 from being coupled through circuit N9 during a calorie rate calculation. The input of NOR gate N11-3 is normally held at logic 0 through resistor R19.

The P1 output of circuit N9 is also applied to the input INVERTER N7-4 of program enable circuit 17. The output of INVERTER N7-4 turns on transistor Q1 and thus energized program memory N3.

The logic 1 at the P1 output of circuit N9 is also applied through diode D2 to INVERTER N7-5 of program sequencer 11. The output of INVERTER N7-5 resets counter N5 to 0. Simultaneously, logic 1 is applied to an input of NAND gate N6-2 which forms an oscillator with NAND gate N6-1. The logic 1 to the input of NAND gate N6-2 gates the oscillator on. The output of the oscillator is applied to the clock input of counter N5. At each positive transition to logic 1 of the oscillator square wave output, the count of counter N5 is advanced one count to a maximum of 16. The oscillator also provides an inhibit signal to circuits N1 and N2 of calculator interface 5.

The four-bit binary count output from counter N5 is applied to the input of program memories N3 and N4 of program memory 9. The four-bit count functions as a memory address to the program memory. As the binary count advances, the process memory provides successive program steps to the keyboard interface 5. In the calorie rate calculation, only program memory N3 has been enabled, and the program steps are provided by program memory N3.

The last step in the program stored in the program memory N3, applies a logic 1 to XOR gate N12-4. This causes the output of XOR gate N12-4 to go to logic 1 which resets the input of circuit N9 and resets the output P1 of N9 to logic 0, thereby disabling the oscillator N6-1 and N6-2 and the program memory N3, which stops the program memory sequence.

The program steps from program memory N3 are applied through the keyboard interface 5 to the calculator keyboard 7. The program steps calculate the calorie burn rate for the particular activity using the activity level rate, modifier constant, and weight value which have been stored in the alpha-numeric calculator memory. Each program step operates the calculator in the same manner as if the keyboard were manually operated by the user. Of course, the program automatically sequence the calculator through the required steps.

Once a calorie burn rate has been stored in the calculator alpha-numeric memory, the device is placed in a mode of operation to continually count at predetermined intervals the number of calories burned in the performance of the activity for which the rate has been calculated and stored. In order to initiate this operation, switch S4 is set to one of the predetermined time intervals which is dependent upon the activity which is being performed. Run-Stop switch S2 is switched to the "Run" position and a logic 1 is applied to NAND gate N6-3 and INVERTER N7-2. A logic 1 at the input of INVERTER N7-2 produces a logic 0 at its output which is applied to the input of XOR gate N12-2. The output of the XOR gate N12-2 switches to logic 0 and counter N8 is enabled. The logic 1 at the input of N6-3 gates the oscillator formed by N6-3 and N6-4. The output of the oscillator is applied to the clock input of counter N8 to advance the counter on each positive transition to logic 1 of the oscillators square wave output signal.

The oscillator frequency is set such that the outputs of the counter N8 go to logic 1 after one or eight minutes depending upon the position of switch S4. In FIG. 2, switch S4 is shown in the eight minute position and thus at the end of eight minutes output P9 of counter N8 goes to logic 1. This causes the output of INVERTER N7-3 to go to logic 0 to turn on LED-1 as a warning that a burn calculation will be executed after approximately a seven second delay. The logic 1 at output P9 of N8 is also coupled through diode D7 to the input of NOR gate N11-3 to prevent the output of NOR gate N11-3 from going to logic 1 if the Net switch S3 is activated.

Approximately seven seconds after the output P9 of the counter N8 goes to logic 1, the output P7 of counter N8 goes to logic 1. Diodes D5 and D6 normally have their cathodes at logic 0 and a voltage applied to the anodes through resistor R20 is below the threshold voltage of NAND gate N10-3. OR gate N12-3 and circuit N9. When the output of counter N8 go to logic 1, the anodes of diodes D5 and D6 go to logic 1. This results in a logic 1 being applied to an input of NAND gate N10-3, to NOR gate N12-3 and to circuit N9. Approximately 1.8 seconds later the output P6 of counter N8 goes to logic 1 and this output is applied to the other input of NOR gate N10-3 which causes its output to go to logic 0. A logic 0 is, therefore, applied to NAND gate N10-4 to cause its output to go to logic 1, to apply a logic 1 reset to counter N8 through XOR gate N12-2. This places all the outputs of counter N8 back to logic 0 with the timing interval starting over. The logic 1 applied to circuit N9 through XOR gate N12-3 and directly applied to circuit N9 is done so for 1.8 seconds to override a stop bit at the beginning at the program sequence.

The logic 1 input to circuit N9 causes the outputs P1 and P2 to go to logic 1. The P1 output enables program memory N3 and oscillator N6-1 and N6-2 in the manner previously described. Counter N5 then sequences the program steps from program memory N3. The output P2 from circuit N9 is applied to program memory N3. The result of this is a set of program steps, different than that for the burn rate calculation, are read from the program memory N3. The last step in this program also resets the control circuit.

The program steps from program memory N3 are applied to the calculator keyboard through the keyboard interface 5. These steps cause the calculator to recall the calorie burn rate which has been stored in the alpha-numeric calculator memory and to add this number to a total calories burned value stored in the calculator. The new total is then substituted for the prior calories burned total.

The control circuit is also used for calculating net calories which is the difference between the total calories burned and the total calories consumed.

The net calories calculation is made by momentarily depressing Net switch S3. This causes a logic 1 to be applied to NOR gate N11-2 the output of which goes to logic 0. The logic 0 is applied to one of the inputs of NOR gate N11-3. If the other input to the NOR gate N11-3 is at logic 0 which indicates that a rate or burn calculation is not being executed, then the output of NOR gate N11-3 goes to logic 1 and this is applied to an input of circuit N9. Output P3 of circuit N9 goes to logic 1 and enables program memory N4 through INVERTER N7-6 and transistor Q2. In addition, the oscillator N6-1 and N6-2 and counter N5 are energized through didoe D1 to start the count sequence. Also, one of the inputs of NOR gate N11-4 goes to logic 1 to prevent operation if the Rate switch S1 is closed.

Counter N5 sequences program memory N4 through the program steps of a net calorie calculation. The program steps are applied to the calculator keyboard through the keyboard interface 5. The program which is applied to the calculator subtracts the calories burned from the calories consumed and displays the difference or net calories on the calculator display.

At the end of the program sequence, if the calories burned is greater than the calories consumed or eaten, a minus sign is displayed on the calculator display. XOR gate N12-1 is used to detect this, with its output producing a square wave that is rectified by diode D3 and filtered by capacitor C2 to produce a logic 1 at the input of NAND gate N10-1. This causes the output of NAND gate N10-1 to go to logic 0 which turns on transistor Q3 and thereby energizes LED-2. LED-2 is self-oscillating and flashes on and off to provide the user with an indication that he has burned more calories that he has eaten. Capacitor C1 discharges in about 4 seconds which causes the output of NAND gate N10-1 to switch back to logic 1 thereby turning off transistor Q3 and LED-2.

The present invention may be embodied in other specific forms without departing from the spirit or essential characteristics thereof. The presently disclosed embodiments are, therefore, to be considered in all respects as illustrative and not restrictive, the scope of the invention being indicated by the appended claims, rather than the foregoing description, and all changes which come within the meaning and range of equivalency of the claims are, therefore, to be embraced therein.

What is claimed is:

1. A calorie monitoring device for calculating the calories burned by a person, the calories consumed by the person and the net difference therebetween, said device comprising:

(a) calculator means for performing arithmetic calculations, said calculator means having a a plurality of memory means for storing alpha-numeric data therein, a keyboard means for entering data into said calculator means and display means for displaying data therein;

(b) program memory means for storing a plurality of control programs for said calculator means;

(c) interface means coupling said program memory means to said calculator means;

(d) program sequencer means, coupled to said program memory means, for controlling the sequence of program steps read from said program memory means;

(e) timer means coupled to said program sequencer means for intiating the operation of said program sequencer means at predetermined time intervals for calculating the calories burned; and (f) switch means for initiating the operation of said device and for selecting one of said plurality of control programs, wherein said switch means includes set-reset logic means coupled between said timer means, said program sequencer means and said program memory means, said set-reset logic means receiving an input from said timer means at the beginning of said predetermined time intervals for the calculation of calories burned and producing an output in response thereto to initiate the operation of said program sequencer means and for receiving an output from said program memory means upon completion of a program therein and producing an output in response thereto for stopping operation of said program sequence means.

2. A calorie monitoring device as set forth in claim 1 wherein a portion of said calculator memory means stores data related to the rate of calories burned for predetermined types of human activity and wherein another portion of said calculator memory means stores data related to the number of calories in predetermined types of foods.

3. A calorie monitoring device as set forth in claim 1, further including program enable means, coupled between said set-reset logic means and said program memory means, for enabling said program memory means in response to an output from said set-reset logic means and for disabling said program memory means when the program therein is completed.

4. A calorie monitoring device as set forth in claim 1, wherein said program memory means comprises read only memories.

5. A calorie monitoring device as set forth in claim 1, wherein said timer means includes switch means for selecting different predetermined intervals.

6. A calorie monitoring device as set forth in claim 1, wherein said switch means includes a rate switch coupled to said set-reset logic means for initiating the operation of said program sequencer means for the calculation of the rate of calories burned by said calculator means.

7. A calorie monitoring device as set forth in claims 1 or 6, wherein said switch means includes a net calorie switch coupled to said set-reset logic means for initiating the calculation of the difference between calories consumed and calories burned by said calculator means.

8. A calorie monitoring device as set forth in claim 7, including minus sign detection means connected to said display means for providing an indication when the difference between calories consumed and calories burned is negative.

9. A net calorie calculating apparatus for calculating the calorie burned by a person, the calories consumed by the person and the difference therebetween said apparatus comprising:
- (a) calculator means for performing mathmatical calculations, said calculator means including keyboard means and display means;
- (b) first memory means coupled to said calculator means, for storing rate data representing the rate of calories burned for different predetermined human activities;
- (c) second memory means coupled to said calculator means, for storing calorie content data representing the number of calories per unit of various predetermined kinds of food;
- (d) program memory means for storing programs for controlling said calculator means for the calculation of calorie burn rate, calories burned, and net calories;
- (e) interface means for coupling said program memory means to said calculator means; and
- (f) control means for controlling the operation of said program memory means, said control means comprising:
  - (i) switch means for selecting the calculation to be performed;
  - (ii) timer means for providing an output at predetermined time intervals;
  - (iii) program sequencer means, coupled to said program memory means, for providing an output to sequence said program memory means through the program steps stored therein; and
  - (iv) set-reset logic means for coupling said switch means and said timer means to said program sequencer means and said program memory means.

10. A net calorie calculating apparatus as set forth in claim 9 wherein said program memory means is a read only memory.

11. A net calorie calculating apparatus as set forth in claim 9 wherein said timer means includes selector means for selecting different predetermined time intervals.

12. A net calorie calculating apparatus as set forth in claim 9 including third memory means, coupled to said calculator means, for storing the total calories consumed by a person, wherein when a person consumes food an alpha-numeric indication thereof is read into said calculator means through said keyboard means and the number of calories corresponding thereto is read from said second memory means and added to the total stored in said third memory means.

13. A net calorie calculating apparatus as set forth in claim 11 including minus sign detection means connected to said display means for providing an indication when the difference between the calories burned and the calories consumed is negative.

* * * * *